(12) United States Patent
Runkler et al.

(10) Patent No.: US 7,197,504 B1
(45) Date of Patent: Mar. 27, 2007

(54) SYSTEM AND METHOD FOR GENERATING DECISION TREES

(75) Inventors: Thomas A. Runkler, Munich (DE); Shounak Roychowdhury, Foster City, CA (US)

(73) Assignee: Oracle International Corporation, Redwood Shores, CA (US)

( * ) Notice: Subject to any disclaimer, the term of this patent is extended or adjusted under 35 U.S.C. 154(b) by 684 days.

(21) Appl. No.: 09/553,956

(22) Filed: Apr. 21, 2000

Related U.S. Application Data

(60) Provisional application No. 60/130,636, filed on Apr. 23, 1999.

(51) Int. Cl.
*G06F 17/00* (2006.01)

(52) U.S. Cl. ............... 707/102; 707/100; 707/101; 707/103 R; 706/45; 706/52

(58) Field of Classification Search ............ 707/3, 707/103 R, 100, 101, 102; 706/45, 52
See application file for complete search history.

(56) References Cited

U.S. PATENT DOCUMENTS

| 5,574,910 A | 11/1996 | Bialkowski et al. | |
|---|---|---|---|
| 6,247,016 B1 * | 6/2001 | Rastogi et al. | ............... 707/101 |

FOREIGN PATENT DOCUMENTS

| JP | 207023 | 8/1993 |
|---|---|---|

OTHER PUBLICATIONS

Hall et al., Generating Fuzzy Rules from Data, Copyright 1996 IEEE, pp. 1757-1762. <http://ieeexplore.ieee.org/iel3/4033/11979/00552635.pdf?isNumber=11979&prod=CNF&arnumber=552635&arSt=1757&ared=1762+vol.3&arAuthor=Hall%2C+L.O%3B+Lande%2C+P.>.*

Shafer et al., SPRINT: A Scalable Parallel Classifer for Data Mining, 22$^{nd}$ VLDB Conference Mumbai, India, 1996, pp. 544-555. <http://www.cis.udel.edu/~agrawal/DataMining/Papers/par_decisiontree1pdf>.*

Choe et al., On the Optimal Choice of Parameters in a Fuzzy C-Means Algorithm, Copyright 1992 IEEE, pp. 349-354. http://ieeexplore.ieee.org/iel5/605/6550/00258640.pdf?isNumber=6550&prod=CNF%arnumber=258640&arSt=349&ared=354&arAuthor=Choe%2C+H.%3B+Jordan.*

Shimoji et al., Data Clustering with Entropical Scheduling, IEEE International Conference, Jun.-Jul. 2, 1994, pp. 2423-2428 vol. 4.*

Choe et al., On the Optimal Choice of Parameters in a Fuzzy C-Means Algorithm, IEEE International Conference on Mar. 8-12, 1992, pp. 349-354.*

Luo et al., "Automated Decision Tree Generation for Object Recognition and Classification," IECON, Sep. 29, 1986, pp. 357-362, IEEE, New York, US.

Jung et al., "A Design Scheme for a Hierarchical Fuzzy Pattern Matching Classifier and its Aplication to the Tire Tread Pattern Recognition," Fuzzy Sets and Systems, Aug. 10, 1994, pp. 311-322, vol. 65 No. 2/03, Elsevier Science Publishers, Amsterdam, NL.

Janikow, "Fuzzy Decision Trees: Issues and Methods," IEEE Transactions on Systems, Man, and Cybernetics, Feb. 1998, pp. 1-14, vol. 28 No. 1.

Patent Office of Japan, "Notification of Reason for Rejection," App. No. 2001-533717, dated Oct. 24, 2006, 5 pages (including 3 page English translation).

* cited by examiner

*Primary Examiner*—Hung Pham
(74) *Attorney, Agent, or Firm*—Hickman Palermo Truong & Becker LLP

(57) ABSTRACT

A decision tree clustering procedure is provided which employs a unified approach to extracting both the decision tree and (preferably fuzzy) clusters. The decision tree is built by subsequent clustering of single dimensions or features, and the choice of the winning separation is based on cluster validity. In one embodiment, the clustering employs a fuzzy c-means (FCM) model and the partition coefficient (PC) to determine the selected separations.

22 Claims, 5 Drawing Sheets

SYSTEM AND METHOD FOR GENERATING DECISION TREES

RELATED APPLICATIONS

This application claims priority from U.S. Provisional Application Ser. No. 60/130,636, filed Apr. 23, 1999, incorporated herein by reference.

FIELD OF THE INVENTION

The present invention relates to data analysis and more particularly to generating decision trees.

BACKGROUND OF THE INVENTION

Data mining, knowledge discovery, and other forms of data analysis involve the extraction of useful information from vast amounts of accumulated data. For example, pharmaceutical companies are creating large databases listing drug compounds and their features, such as which diseases that are effectively treated by which drug compound and what are the drug compound's side-effects. Given the large number of different drug compounds, it is difficult to manually analyze this data to ascertain useful patterns, such as determining what group of drugs are more or less effective in treating each of a group of diseases, especially when the desired groupings of drugs and diseases are not identified beforehand.

Conventional data mining techniques use pattern recognition and probabilistic analyses to generate decision trees. A decision tree is a data structure that contains a hierarchical arrangement of rules that successively indicates how to classify an object into a plurality of classes. More specifically, each object is characterized by a number of attributes, and each rule in the decision tree tests the value of one of the attributes. Decision trees separate out data into sets of rules that are likely to have a different effect on a target variable. For example, one might want to find the characteristics of a drug compound and its method of administration that are likely to be effective in treating a particular disease. These characteristics can be translated into a set of rules.

FIG. 5 depicts an exemplary decision tree 500 that represents how to treat a hypothetical medical condition for a patient. The exemplary decision tree 500 comprises two branch nodes 510 and 530, three leaf nodes 520, 540, and 550, and arcs 512, 514, 532, and 534.

Each of the branch nodes 510 and 530 represents a "rule" or condition that indicates how to choose between a number of possible values for a particular attribute of the patient. The possible values that the attribute may take are indicated by the arcs 512, 514, 532, and 534. When a choice among the possible values is made, the corresponding arc is taken to reach a leaf node or another branch node. One of the branch nodes 510 is designated as the "root" node, which is the starting point of the decision tree.

In the example, root branch node 510 is labeled "AGE?" and indicates that the age of the patient is tested. Arc 512, which connects branch node 510 to leaf node 520, is labeled "<=12?" indicating that leaf node 520 is to be reach if the age of the patient is less than or equal to 12. On the other hand, arc 514 connects branch node 510 to branch node 530 and is labeled ">12?", which indicates that branch node 530 is to be reached if the age of the patient is greater than 12. Branch node 530 is labeled "TEMP?" to indicate that the body temperature of the patient is tested. If the body temperature of the patient is less than or equal to 102° (indicated by arc 532), then leaf node 540 is reached; otherwise, if the body temperature of the patient is greater than 102° (indicated by arc 5334), then leaf node 550 is reached.

The leaf nodes 520, 540, and 550 represent a "decision" or classification of the object. In this example, the decision is the treatment to be administered to the patient. At leaf node 520, the decision is to use 20 mg of drug X; at leaf node 540, the decision is to use 40 mg of drug X; and at leaf node 550, the decision is to use 10 mg of drug Y.

The exemplary decision tree 500 may be used to determine which treatment to be administered to a patient by starting at the "root" node, testing the attribute of the patients to select an arc and follow the arc until a leaf node is reached. In the example, suppose a 10 year old child with a temperature of 98.6° is to be treated. Starting at root branch node 510, the age of the patient is tested. Since the 10 year old is less than 12 years of age, arc 512 is followed to reach leaf node 520. Therefore, 20 mg of drug X is prescribed to the 10 year old. As another example, suppose the patient is a 32-year with a 105° fever. Starting at root branch node 510, the age of the patient is tested. Since the 32-year old's age is greater than 12, arc 514 is followed to branch node 530 where the body temperature of the patient is tested. Since the patient has a 105° fever, arc 534 is followed to reach leaf node 550, which indicates that 10 mg of drug Y is to be administered.

Decision tree induction refers to the process of determining how to build the decision tree from a set of training data. In particular, a decision tree is built by successively identifying which attributes to test first and which attributes to test later, if at all. A common conventional approach to build decision trees is known as "Induction of Decision Trees" or ID3. The ID3 is a recursive algorithm that starts with a set of training objects that belong to a set of predefined classes. If all the objects belong to a single class, then there is no decision to make and a leaf node is created and labeled with the class. Otherwise, a branch node is created and the attribute with the highest "information gain" is selected if that attribute were used to discriminate objects at the branch node. The information gain is calculated by finding the average entropy of each attribute.

A problem with conventional decision trees such as those produced by ID3 is that such decision trees are rigid, inflexible, and brittle. In the drug effectiveness example, conventional decision trees impose an "either-or" or binary approach to the data, even though different drugs have varying degrees of effectiveness. For example, data values close to the border of a crisp range in a decision tree are apt to be misclassified due to the imprecision of real-world data. Accordingly, there has been a number of attempts to apply the concepts of "fuzzy logic" to decision trees.

Fuzzy logic was introduced in the 1960's as a means for modeling the uncertainty of the real world. Rather than classifying an object as either a full member of one class or not a member at all, fuzzy logic employs a "membership function" between 0.0 and 1.0 to represent the degree to which the object belongs to the class. For example, rather than categorize a patient's age as "twelve years and below" and "above twelve years," two fuzzy sets, Young and Old, can be employed, such that a two-year old may have a membership function in the Young fuzzy set $\mu_{Young}(2)=0.99$ but a membership function in the Old fuzzy set $\mu_{Old}(2)=0.01$. Conversely, a retired person at 65 years of age, may have a Young membership function of $\mu_{Young}(65)=0.13$ and an Old membership function of $\mu_{Old}(65)=0.87$. For a teenager, however, the membership functions are not so extreme;

for example, a 13-year may have membership functions of $\mu_{Young}(13)=0.45$ and $\mu_{Old}(13)=0.55$.

One attempt to combine fuzzy logic with classical, crisp decision trees is known as FID3, in which the user defines the membership functions in each of the predefined classes for all of the training data. Each membership function can serve as an arc label of a fuzzy decision. As in ID3, FID3 generates its decision tree by maximizing information gains. The decision of the fuzzy decision tree is also a fuzzy variable, indicating the memberships of a tested object in each of the possible classifications. In the example of FIG. 5, the arcs 512 and 514 emanating from branch node 510 could be fuzzified by a membership function on a Young fuzzy set and an Old fuzzy set, respectively. For example, arc 512 could be the test $\mu_{Young}(X_i)<0.5$ or other value that maximizes the information gain. For the arcs 532 and 534, the respective fuzzy sets could be Normal and Feverish, respectively. A result with a 0.20 membership in the class at leaf node 520 and 0.80 membership in the class at leaf node 540, for example, might suggest using 36 mg of drug X.

One disadvantage with FID3 is that the membership functions in each of the attributes for all of the training data must be specified beforehand by the user. For data with a high number of attributes or dimensions, however, determining the membership functions is typically a difficult task, requiring intensive involvement by experts. In addition, the fuzzy sets themselves may not even be known beforehand and require further investigation.

Therefore, there is a need for a data analysis technique that is capable of handling real-world or "fuzzy" data in a flexible manner. There is also a need for a technique in which the groupings of the data or other a priori information, such as fuzzy membership functions, need not be supplied beforehand.

SUMMARY OF THE INVENTION

These and other needs are addressed by the present invention, in which the data are dynamically clustered while a decision tree is generated. In one embodiment, the data are clustered using a fuzzy clustering analysis, which generates the membership functions on the fly, without requiring the user to predefine sets or calculate the membership functions beforehand.

Accordingly, one aspect of the invention involves a method and software for generating a decision tree for data characterized by several features, in which several fuzzy cluster analyses are performed along each of the features to calculate a maximal partition coefficient and a corresponding set of one or more fuzzy clusters. The feature corresponding to the maximal partition coefficient is selected, and the decision tree is built based on the corresponding set of one or more fuzzy clusters. By performing a fuzzy cluster analysis, real world data is better accounted for.

Another aspect of the invention relates to a method and software for generating a decision tree for data that is characterized by several features, in which several cluster analyses are performed along each of the features to calculate a maximal cluster validity measure. One of the features corresponding to the maximal cluster validity measure is selected, and the data is subdivided into one or more groups based on the selected feature. Then, the decision tree is built based on the one or more groups. By performing cluster analyses to calculate a maximal cluster validity, the decision tree can correspond to an optimal cluster separability.

Still another aspect of the invention pertains to a method and software for generating a decision tree for data characterized by several features (e.g. dimensions or attributes), in which one of the features is selected. A cluster analysis along the selected feature is performed to group the data into one or more clusters, and the decision tree is built based on the one or more clusters. By performing a cluster analysis, the data need not be pre-analyzed to determine the various possible sets in which the data may be grouped.

Still other objects and advantages of the present invention will become readily apparent from the following detailed description, simply by way of illustration of the best mode contemplated of carrying out the invention. As will be realized, the invention is capable of other and different embodiments, and its several details are capable of modifications in various obvious respects, all without departing from the invention. Accordingly, the drawing and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DESCRIPTION OF THE PREFERRED EMBODIMENT

A method and apparatus for generating decision trees is described. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Hardware Overview

Figure 1:
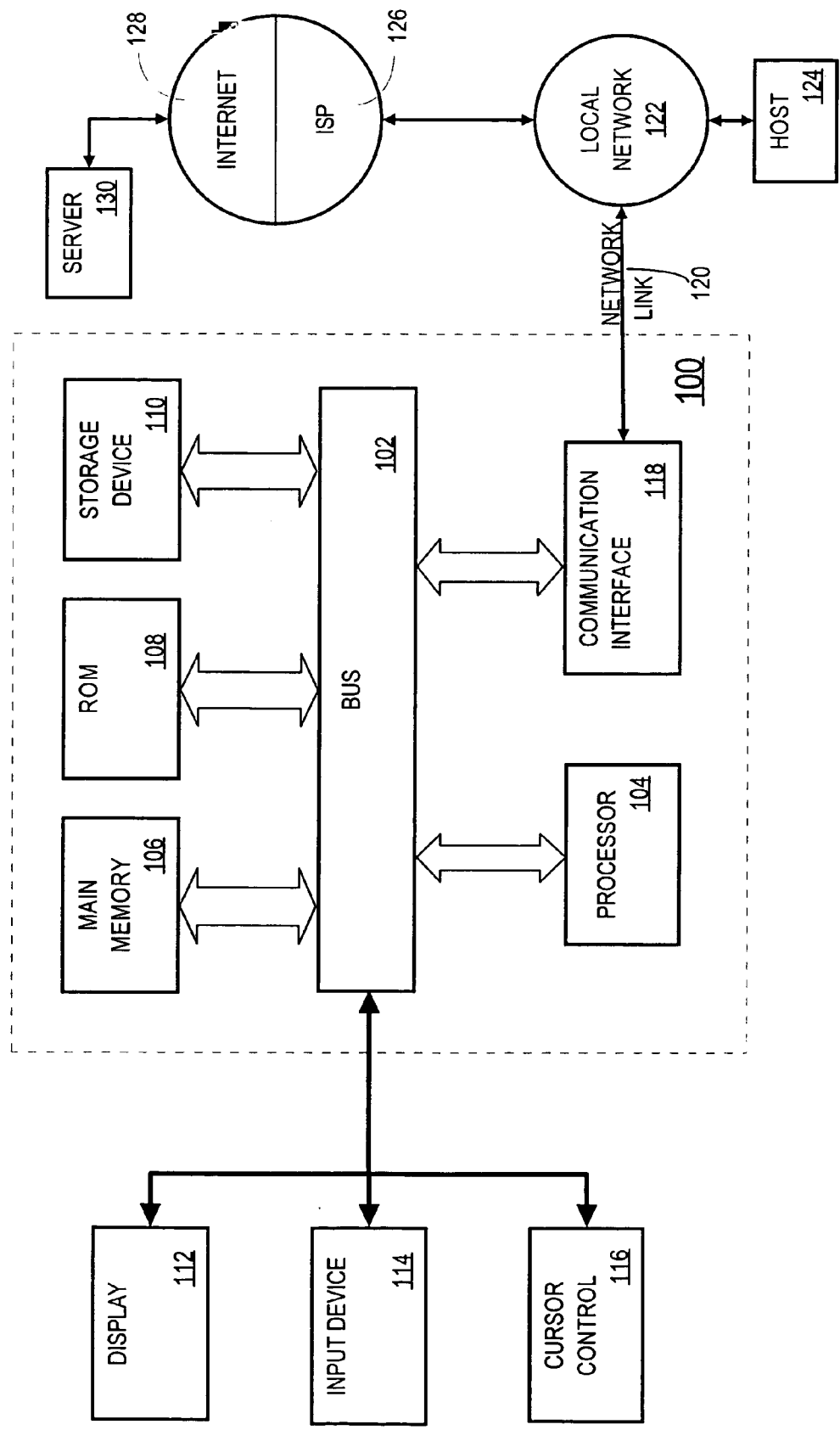
FIG. 1 depicts a computer system upon which an embodiment of the present invention can be implemented.

FIG. 1 is a block diagram that illustrates a computer system 100 upon which an embodiment of the invention may be implemented. Computer system 100 includes a bus 102 or other communication mechanism for communicating information, and a processor 104 coupled with bus 102 for processing information. Computer system 100 also includes a main memory 106, such as a random access memory (RAM) or other dynamic storage device, coupled to bus 102 for storing information and instructions to be executed by processor 104. Main memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT), for displaying information to a computer user. An input device 114, including alphanumeric and other keys, is coupled to bus 102 for communicating information and command selections to processor 104. Another type of user input device is cursor control 116, such as a mouse, a trackball, or cursor direction keys for communicating direction information and command selections to processor 104 and for controlling cursor movement on display 112. This input device typically has two degrees of freedom in two axes, a first axis (e.g., x) and a second axis (e.g., y), that allows the device to specify positions in a plane.

The invention is related to the use of computer system 100 for generating decision trees. According to one embodiment of the invention, generating decision trees is provided by computer system 100 in response to processor 104 executing one or more sequences of one or more instructions contained in main memory 106. Such instructions may be read into main memory 106 from another computer-readable medium, such as storage device 110. Execution of the sequences of instructions contained in main memory 106 causes processor 104 to perform the process steps described herein. One or more processors in a multi-processing arrangement may also be employed to execute the sequences of instructions contained in main memory 106. In alternative embodiments, hard-wired circuitry may be used in place of or in combination with software instructions to implement the invention. Thus, embodiments of the invention are not limited to any specific combination of hardware circuitry and software.

The term "computer-readable medium" as used herein refers to any medium that participates in providing instructions to processor 104 for execution. Such a medium may take many forms, including but not limited to, non-volatile media, volatile media, and transmission media. Non-volatile media include, for example, optical or magnetic disks, such as storage device 110. Volatile media include dynamic memory, such as main memory 106. Transmission media include coaxial cables, copper wire and fiber optics, including the wires that comprise bus 102. Transmission media can also take the form of acoustic or light waves, such as those generated during radio frequency (RF) and infrared (IR) data communications. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 104 for execution. For example, the instructions may initially be borne on a magnetic disk of a remote computer. The remote computer can load the instructions into its dynamic memory and send the instructions over a telephone line using a modem. A modem local to computer system 100 can receive the data on the telephone line and use an infrared transmitter to convert the data to an infrared signal. An infrared detector coupled to bus 102 can receive the data carried in the infrared signal and place the data on bus 102. Bus 102 carries the data to main memory 106, from which processor 104 retrieves and executes the instructions.

The instructions received by main memory 106 may optionally be stored on storage device 110 either before or after execution by processor 104.

Computer system 100 also includes a communication interface 118 coupled to bus 102. Communication interface 118 provides a two-way data communication coupling to a network link 120 that is connected to a local network 122. For example, communication interface 118 may be an integrated services digital network (ISDN) card or a modem to provide a data communication connection to a corresponding type of telephone line. As another example, communication interface 118 may be a local area network (LAN) card to provide a data communication connection to a compatible LAN. Wireless links may also be implemented. In any such implementation, communication interface 118 sends and receives electrical, electromagnetic or optical signals that carry digital data streams representing various types of information.

Network link 120 typically provides data communication through one or more networks to other data devices. For example, network link 120 may provide a connection through local network 122 to a host computer 124 or to data equipment operated by an Internet Service Provider (ISP) 126. ISP 126 in turn provides data communication services through the worldwide packet data communication network, now commonly referred to as the "Internet" 128. Local network 122 and Internet 128 both use electrical, electromagnetic or optical signals that carry digital data streams. The signals through the various networks and the signals on network link 120 and through communication interface 118, which carry the digital data to and from computer system 100, are exemplary forms of carrier waves transporting the information.

Computer system 100 can send messages and receive data, including program code, through the network(s), network link 120, and communication interface 118. In the Internet example, a server 130 might transmit a requested code for an application program through Internet 128, ISP 126, local network 122 and communication interface 118. In accordance with the invention, one such downloaded application provides for generating decision trees as described herein. The received code may be executed by processor 104 as it is received, and/or stored in storage device 110, or other non-volatile storage for later execution. In this manner, computer system 100 may obtain application code in the form of a carrier wave.

Fuzzy Clustering

One aspect of the present invention stems from the realization that data set itself contains the information that can be used to obtain reasonable membership functions. Thus, both the decision tree and the membership functions can be automatically extracted from the data set. In one embodiment of the present invention, a fuzzy c-means (FCM) clustering approach is used to extract the membership functions from the data, although other forms of fuzzy clustering may be employed in various embodiments of the present invention.

The FCM model may be defined as the minimization of the objective function $J_{FCM}$ for a given data set $X=\{x_i\}$, $i \in 1 \ldots n$ with dimensions $l \in 1 \ldots p$, and a fuzziness parameter $m \in (1, \infty)$:

$$J_{FCM}(U, V; X) = \sum_{k=1}^{n} \sum_{i=1}^{c} u_{ik}^m |x_k - v_i|^2, \qquad (1)$$

where $U = \{u_{ik}\}$, $V = \{v_i\}$, $u_{ik} \in [0, 1]$ is the membership of $x_k$ in the $i^{th}$ cluster of c clusters, $i \in 1 \ldots c$, $k \in 1 \ldots n$, with $\Sigma u_{ik} = 1$, for all $k \in 1 \ldots n$, and $v_i$ is the center of the $i^{th}$ cluster, $i \in 1 \ldots c$, and m is typically 2. In one implementation, the FCM model is optimized by alternating optimization (AO) through the necessary extrema of $J_{FCM}$, however other optimization techniques may be employed.

With the AO technique for FCM, memberships $u_{ik}$ and cluster centers $v_i$ are alternatingly updated as:

$$u_{ik} = 1 \bigg/ \sum_{j=1}^{c} \left( \frac{|x_k - v_i|}{|x_k - v_j|} \right)^{\frac{2}{m-1}} \qquad (2)$$

and $$v_i = \frac{\sum_{k=1}^{n} u_{ik}^m x_k}{\sum_{k=1}^{n} u_{ik}^m}, \qquad (3)$$

until subsequent estimations V and V* of the cluster centers satisfy $\max_{i \in 1 \ldots c} \max_{l \in 1 \ldots p} (v_i^{(l)} - v_i^{(l*)}) < v_{th}$, where $v_{th}$ is a threshold parameter.

The continuous membership functions $\mu_i^{(l)}$: IR→[0, 1], $i \in 1 \ldots c$, $l \in 1 \ldots p$, can be obtained by projection and subsequent interpolation or approximation of the $u_{ik}$ memberships, or simply by inserting the projections $v_i^{(l)}$ of the cluster centers $v_i$ into:

$$\mu_i^{(l)}(x^{(l)}) = 1 \bigg/ \sum_{j=1}^{c} \left( \frac{|x^{(l)} - v_i^{(l)}|}{|x^{(l)} - v_j^{(l)}|} \right)^{\frac{2}{m-1}}. \qquad (4)$$

Generating a Decision Tree

Figure 2:
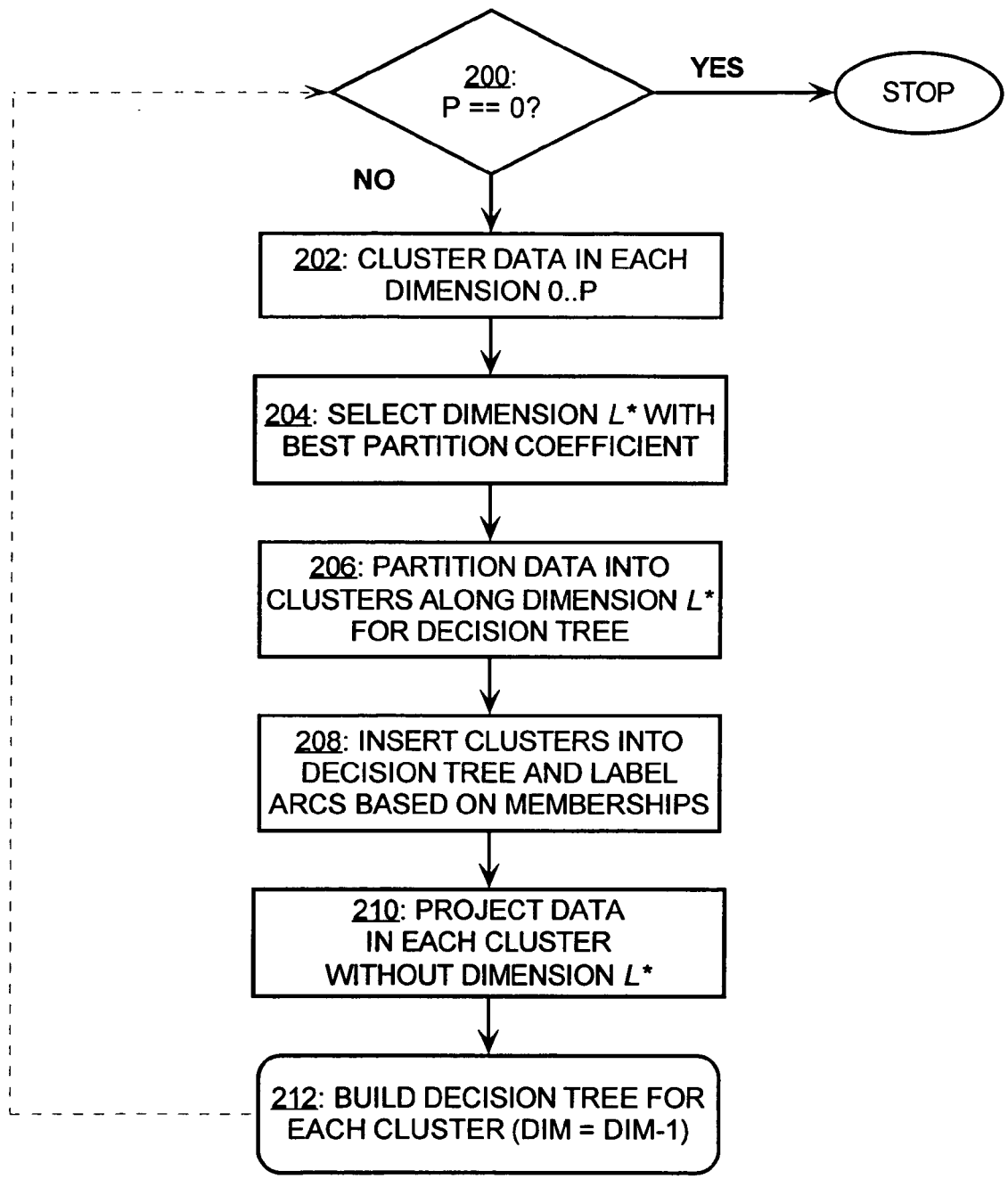
FIG. 2 is a flowchart illustrating the operation of one embodiment of the present invention.

In accordance with one embodiment of the invention, the extraction of membership functions is obtained by clustering while generating a decision tree by induction. At the beginning of operation, the decision tree starts with a root node that is associated with the data set. For each node N associated with data (e.g. starting from the root node), the steps illustrated in FIG. 2 are performed. For purposes of explanation, the operation of this embodiment of the present invention is illustrated to an exemplary data set 300 shown in FIG. 3 using the parameters, m=2, c=4, $v_{th}$=10$^{-10}$, and a domain limit threshold $r_{th}$=0.3, as explained in greater detail hereinafter. In addition, the result of this working example is depicted as decision tree 400 of FIG. 4.

At step 200, the number of remaining dimensions p is checked. If zero dimensions remain, then there is no further subdivision to be made and the current node is made a leaf node. While the term "dimension" is used in this discussion because the point data in the working example are continuous, the present invention is not so limited, and the described approach may be applied more generically to features of the data, which can be continuous dimension data as well as nominal attribute data. Dimensional data typically refers to continuous or quantized measurements, such as length, time, charge, temperature, mass, energy, etc. Nominal attribute data typically refers to one element chosen from a finite set, for example, male/female, etc.

Figure 3:
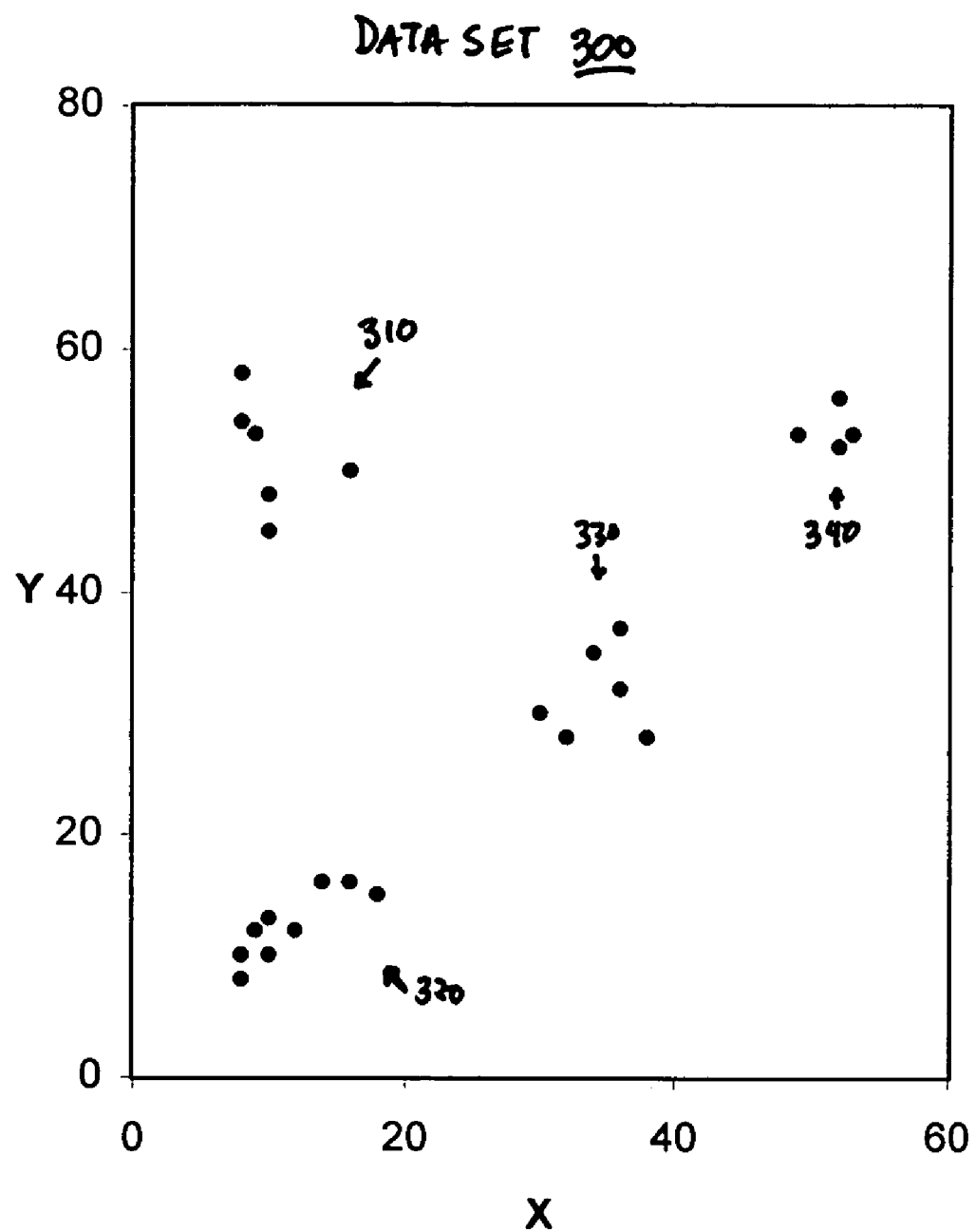
FIG. 3 is a graph of an exemplary data set used to illustrate the operation of one embodiment of the present invention.

Referring to FIG. 3, data set 300 is comprises 29 two-dimensional points, which form four clearly visible cluster, cluster 310 of six points in the upper-left corner, cluster 320 of nine points in the lower-left corner, cluster 330 of six points in the middle, and cluster 340 of four points in the upper-right corner. By visual inspection, the clusters can be separated into a cluster pair on the left and two single clusters in the middle and right, respectively, with the vertical lines x=25 and x=45. The cluster pair on the left, comprising clusters 310 and 320, can further be separated by a horizontal line y=30. In the working example, there are two remaining dimensions, x and y, thus execution proceeds to step 202.

At step 202, the data in each dimension (e.g. x and y) are clustered and a partition coefficient, which quantifies the goodness of the clustering, is computed for each dimension as a measure of cluster validity or how well separated the clusters are. In one implementation, fuzzy c-means clustering may be employed, but other forms of fuzzy clustering such as fuzzy k-means may be employed. In a fuzzy c-means clustering approach, the objective function $J_{FCM}$ is minimized for a given number of clusters c. Thus, fuzzy clustering is performed for several different clustering numbers (for example, up to a c=4 clusters) leading to partitions $U_c^{(l)}$ and a partition coefficient $PC(U_c^{(l)})$ is calculated.

In one embodiment, $PC(U_c^{(l)})$ is calculated for c>1 as follows:

$$PC(U_c^{(l)}) = \frac{1}{n} \sum_{k=1}^{n} \sum_{i=1}^{c} \left( u_{ikc}^{(l)} \right)^2. \qquad (5)$$

Under certain circumstances, the data components might not possess any cluster structure at all. Thus, there is a need for testing the data to determine if the best clustering is a single clustering. In one embodiment, the domain limits of the data are tested, and if the domain of the data in a cluster in the dimension ($\xi_{max} - \xi_{min}$) fall within a predetermined fraction of the of the domain of the entire data set ($x_{max} - x_{min}$), then the data are considered to constitute a single cluster. More specifically, the following test can be performed:

$$\frac{\xi_{max}^{(l)} - \xi_{min}^{(l)}}{x_{max}^{(l)} - x_{min}^{(l)}} < r_{th}. \qquad (6)$$

where $r_{th}$ is a configurable threshold parameter (e.g. 0.3). If the data should be considered to be in a single cluster, then the partition coefficient is set to 1.0 to be greater than the partition coefficients of plural clusters.

In the working example, the clustering in the x-dimension with the maximal partition coefficient of 0.94 has three clusters, and the clustering in the y-dimension with the maximal partition coefficient of 0.93 also has three clusters.

At step 204, the dimension l* with the best partition coefficient is selected. The best partition is obtained for the maximum $PC(U_{c*}^{(l*)})=\max_{c,l}\{PC(U_c^{(l)})\}$. In the working example, the x-dimension is chosen because the partition coefficient of the x-dimension (0.94) is greater than the partition coefficient of the y-dimension (0.93).

At step 206, the data is then partitioned into the c* clusters along the selected dimension l*. These subsets are inserted (step 208) into the decision tree by constructing c* arcs at the current node N with the labels $x^{(l*)}<b_1^{(l*)}$, $b_1^{(l*)}<x_1^{(l*)}<b_2^{(l*)}$, . . . , $b_{c*-2}^{(l*)}<x^{(l*)}<b_{c*-1}^{(l*)}$, $b_{c*-1}^{(l*)}<x^{(l*)}$. The boundaries $b_i^{(l*)}$, i∈1 . . . c*-1, are determined so that the adjacent membership functions defined by (4) are equal or, assuming without loss of generality that the cluster centers are sorted:

$$\mu_i^{(l*)}(b_i^{l*})=\mu_{i+1}^{(l*)}(b_i^{(l*)}) \quad (7)$$

$$\Rightarrow b_i^{(l*)} = \frac{v_i^{(l*)} + v_{i+1}^{(l*)}}{2}. \quad (8)$$

Figure 4:
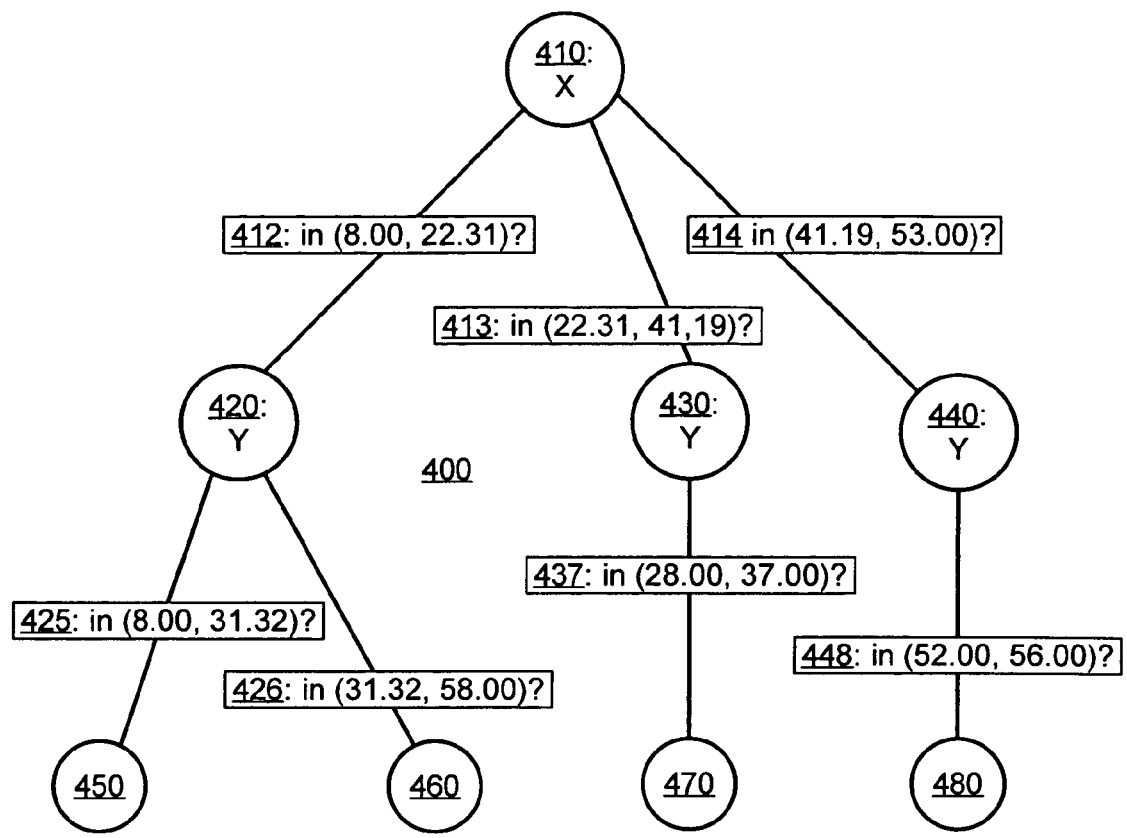
FIG. 4 is a schematic diagram of an exemplary decision tree produced by one embodiment of the present invention.
Figure 5:
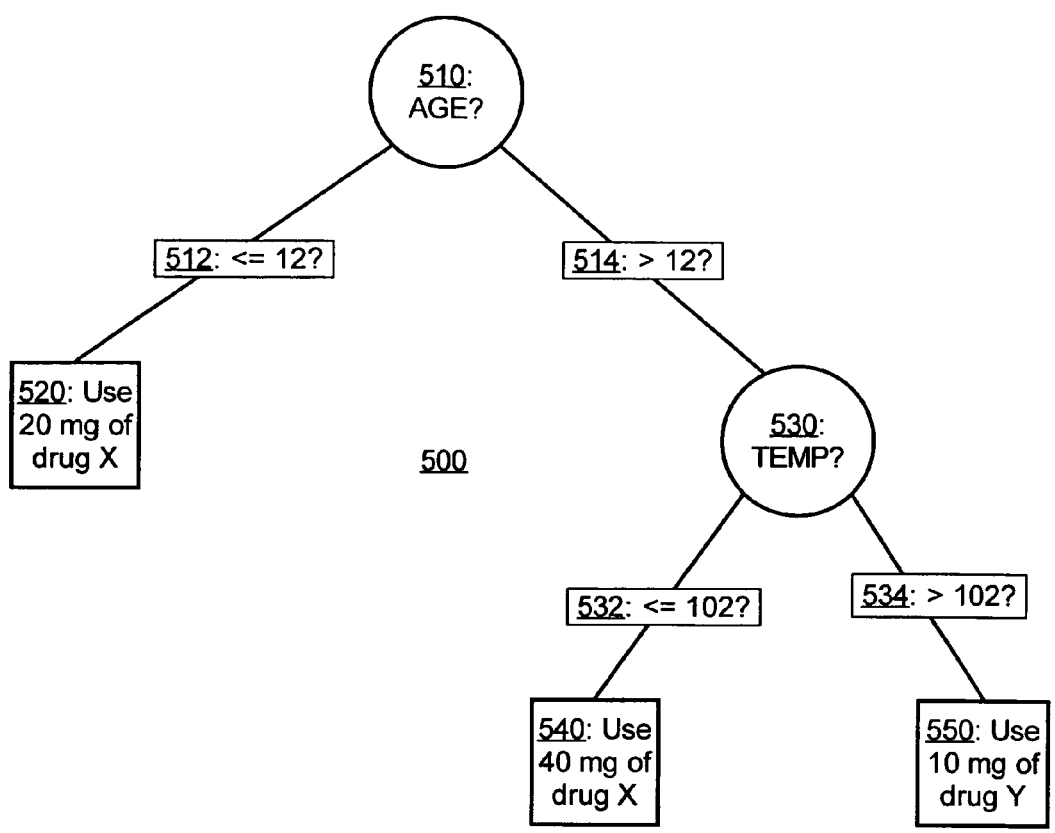
FIG. 5 is a schematic diagram of a decision tree.

In the working example with reference to FIG. 4, the x-dimension was selected. Thus, branch node 410 at the root of the decision tree is labeled to indicate that the x-dimension is tested at node 410. Each arc 412, 413, and 414 from node 410 to respective nodes 420, 430, and 440 is labeled with the borders (8.00, 22.31), (22.31, 41.19), and (41.19, 53.00), respectively.

Referring back to FIG. 2, at step 210, the data are projected in each cluster but for the selected dimension l*. In other words, each datum $x_i$ contains a subset of the p-1 dimensional projection of the data set X that fulfills the condition label $b_{i-1}^{(l*)}<x^{(l*)}<b_i^{(l*)}$, where $b_0^{(l*)}=-\infty$ and $b_{c*}^{(l*)}=+\infty$. In the working example, the x-coordinates are removed from the data, leaving only the y-coordinates, because the x-dimension was the dimension selected in step 204.

At step 212, the process of steps 200–210 is repeated recursively for each cluster, until there is no dimension or data left. In the working example with reference to FIG. 4, the recursive application of this process results in two additional leaf nodes 450 and 460, corresponding to clusters 320 and 310 respectively. The arcs 425 and 426 from branch node 420 to respective leaf nodes 450 and 460 are labeled (8.00, 31.32) and (31.32, 58.00), respectively. The recursive calls for the other subsets corresponding to branch nodes 430 and 440, however, do not result in further splitting into clusters because the test of inequality (6) held. Rather, a single arc 437 emanates from the branch node 430 to leaf node 470, and a single arc 448 emanates from the branch node 440 to leaf node 480.

The result of this embodiment on the exemplary data set 300 is therefore a decision tree 400 with four leaf nodes 450, 460, 470, and 480, each corresponding to the four clusters 320, 310, 330, and 340, respectively, in the data set 300 that was evident by visual inspection. Thus, the corresponding crisp partition, moreover, is exactly the same as the visually obtained partitions, i.e. the points $x_k \in X$ belong to the same (crisp) classes. The borderlines, x=22.31, x=41.19, and y=31.32, however, are slightly different than that produced by visual inspection, because the borderlines were automatically determined from the clustering results. The automatically generated borderlines, moreover, are set up to produce optimal cluster separability.

Accordingly, a decision tree clustering procedure has been described which employs a unified approach to extracting both the decision tree and the (crisp or fuzzy) clusters. The decision tree is built by subsequent clustering of single dimensions or features, and the choice of the winning separation is based on cluster validity. In one embodiment, the clustering employs a fuzzy c-means (FCM) model and the partition coefficient (PC) to determine the selected separations. Use of the partition coefficient as the cluster validity measure produces results that are good or optimal with respect to cluster separability. Other optimality conditions, however, can be incorporated by choosing other validity measures, and clustering models other than FCM can be employed for generating decisions trees. For example, the use of a hard c-means (HCM) model instead of FCM, for example, leads to crisp decision trees.

While this invention has been described in connection with what is presently considered to be the most practical and preferred embodiment, it is to be understood that the invention is not limited to the disclosed embodiment, but on the contrary, is intended to cover various modifications and equivalent arrangements included within the spirit and scope of the appended claims.

What is claimed is:

1. A computer-implemented method for refining a node of a decision tree associated with a plurality of data characterized by a plurality of features, comprising:

selecting a feature from among the features characterizing the data associated with the node;

performing a cluster analysis along the selected feature to group the data into one or more clusters based on distances between the data and respective one or more centers of the one or more clusters;

constructing one or more arcs of the decision tree at the node respectively for each of the one or more clusters;

projecting the data in each of the clusters, wherein the projected data are characterized by the plurality of the features but for the selected feature; and recursively performing the steps of selecting a feature and performing the cluster analysis on the projected data in each of the clusters, wherein the step of performing the cluster analysis includes the step of performing a hard cluster analysis.

2. A computer-implemented method for refining a node of a decision tree associated with a plurality of data characterized by a plurality of features, comprising:

selecting a feature from among the features characterizing the data associated with the node;

performing a cluster analysis along the selected feature to group the data into one or more clusters;

constructing one or more arcs of the decision tree at the node respectively for each of the one or more clusters;

projecting the data in each of the clusters, wherein the projected data are characterized by the plurality of the features but for the selected feature; and recursively performing the steps of selecting a feature and performing the cluster analysis on the projected data in each of the clusters, wherein the step of performing the cluster analysis along the selected feature to group the data into one or more clusters includes the steps of:

calculating a domain ratio of a difference in domains limits of the data over a difference in domain limits of a superset of the data;

determining whether the domain ratio has a predetermined relationship with a predetermined threshold; and if the domain ratio has the predetermined relationship with the predetermined threshold, then grouping the data into a single cluster.

3. The method according to claim 2, wherein the step of determining whether the domain ratio has the predetermined relationship with the predetermined threshold includes the step of determining whether the domain ratio is less than the predetermined threshold.

4. A computer-implemented method for generating a decision tree for a plurality of data characterized by a plurality of features, comprising:

performing a plurality of cluster analyses along each of the features to calculate a plurality of respective partition coefficients based on membership functions of the data for one or more clusters in respective said cluster analyses;

selecting the one of the features corresponding to a maximal partition coefficient from among the partition coefficients;

subdividing the data into one or more groups based on the selected feature; and building the decision tree based on the one or more groups.

5. The method according to claim 4, wherein the step of performing the cluster analyses includes the step of performing a plurality of fuzzy cluster analyses.

6. The method according to claim 4, wherein the step of performing the fuzzy cluster analyses includes the step of performing a plurality of fuzzy c-means analyses.

7. The method according to claim 4, wherein the step of performing the cluster analyses includes the step of performing a plurality of hard cluster analyses.

8. The method according to claim 4, wherein the step of performing the cluster analyses includes the steps of:

calculating a domain ratio of a difference in domains limits of the data over a difference in domain limits of a superset of the data;

determining whether the domain ratio has a predetermined relationship with a predetermined threshold; and if the domain ratio has the predetermined relationship with the predetermined threshold, then grouping the data into a single cluster.

9. The method according to claim 4, wherein building the decision tree based on the one or more groups includes the steps of:

projecting the data in each of the groups, wherein the projected data are characterized by the plurality of the features but for the selected feature; and recursively performing the steps of selecting a feature, comprising selecting a new one of the features corresponding to a new maximal partition coefficient and subdividing the data into one or more new groups based on the selected new feature.

10. A computer-implemented method for generating a decision tree for a plurality of data characterized by a plurality of features, comprising:

performing a plurality of fuzzy cluster analyses along each of the features to calculate a maximal partition coefficient and a corresponding set of one or more fuzzy clusters, said maximal partition coefficient corresponding to one of the features;

selecting the one of the features corresponding to the maximal partition coefficient; and building the decision tree based on the corresponding set of one or more fuzzy clusters and the selected one of the features.

11. The method of claim 10 wherein the maximal partition coefficient is based on membership functions of the data for the set of one or more clusters.

12. A computer-readable medium bearing instructions for refining a node of a decision tree associated with a plurality of data characterized by a plurality of features, said instructions being arranged to cause one or more processors upon execution thereby to perform the steps of:

selecting a feature from among the features characterizing the data associated with the node;

performing a cluster analysis along the selected feature to group the data into one or more clusters based on distances between the data and respective one or more centers of the one or more clusters;

constructing one or more arcs of the decision tree at the node respectively for each of the one or more clusters;

projecting the data in each of the clusters, wherein the projected data are characterized by the plurality of the features but for the selected feature; and recursively performing the steps of selecting a feature and performing the cluster analysis on the projected data in each of the clusters, wherein the step of performing the cluster analysis includes the step of performing a hard cluster analysis.

13. A computer-readable bearing instructions for refining a node of a decision tree associated with a plurality of data characterized by a plurality of features, said instructions being arranged to cause one or more processors upon execution thereby to perform the steps of:

selecting a feature from among the features characterizing the data associated with the node;

performing a cluster analysis along the selected feature to group the data into one or more clusters;

constructing one or more arcs of the decision tree at the node respectively for each of the one or more clusters;

projecting the data in each of the clusters, wherein the projected data are characterized by the plurality of the features but for the selected feature; and recursively performing the steps of selecting a feature and performing the cluster analysis on the projected data in each of the clusters, wherein the step of performing the cluster analysis along the selected feature to group the data into one or more clusters includes the steps of:

calculating a domain ratio of a difference in domains limits of the data over a difference in domain limits of a superset of the data;

determining whether the domain ratio has a predetermined relationship with a predetermined threshold; and if the domain ratio has the predetermined relationship with the predetermined threshold, then grouping the data into a single cluster.

14. The computer-readable medium according to claim 13, wherein the step of determining whether the domain ratio has the predetermined relationship with the predetermined threshold includes the step of determining whether the domain ratio is less than the predetermined threshold.

15. A computer-readable medium bearing instructions for generating a decision tree for a plurality of data characterized by a plurality of features, said instructions being arranged to cause one or more processors upon execution thereby to perform the steps of:

performing a plurality of cluster analyses along each of the features to calculate a plurality of respective partition coefficients based on membership functions of the data for one or more clusters in respective said cluster analyses;

selecting the one of the features corresponding to a maximal partition coefficient from among the partition coefficients;

subdividing the data into one or more groups based on the selected feature; and building the decision tree based on the one or more groups.

16. The computer-readable medium according to claim 15, wherein the step of performing the cluster analyses includes the step of performing a plurality of fuzzy cluster analyses.

17. The computer-readable medium according to claim 15, wherein the step of performing the fuzzy cluster analyses includes the step of performing a plurality of fuzzy c-means analyses.

18. The computer-readable medium according to claim 15, wherein the step of performing the cluster analyses includes the step of performing a plurality of hard cluster analyses.

19. The computer-readable medium according to claim 15, wherein the step of performing the cluster analyses includes the steps of:

calculating a domain ratio of a difference in domains limits of the data over a difference in domain limits of a superset of the data;

determining whether the domain ratio has a predetermined relationship with a predetermined threshold; and if the domain ratio has the predetermined relationship with the predetermined threshold, then grouping the data into a single cluster.

20. The computer-readable medium according to claim 15, wherein building the decision tree based on the one or more groups includes the steps of:

projecting the data in each of the groups, wherein the projected data are characterized by the plurality of the features but for the selected feature; and recursively performing the steps of selecting a feature, comprising selecting a new one of the features corresponding to a new maximal partition coefficient and subdividing the data into one or more new groups based on the selected new feature.

21. A computer-readable medium bearing instructions for generating a decision tree for a plurality of data characterized by a plurality of features, said instructions being arranged to cause one or more processors upon execution thereby to perform the steps of:

performing a plurality of fuzzy cluster analyses along each of the features to calculate a maximal partition coefficient and a corresponding set of one or more fuzzy clusters, said maximal partition coefficient corresponding to one of the features;

selecting the one of the features corresponding to the maximal partition coefficient; and building the decision tree based on the corresponding set of one or more fuzzy clusters and the selected one of the features.

22. The computer-readable medium of claim 21, wherein the maximal partition coefficient is based on membership functions of the data for the set of one or more clusters.

* * * * *